United States Patent
Chen et al.

(10) Patent No.: US 8,828,958 B2
(45) Date of Patent: Sep. 9, 2014

(54) SINGLE-STRANDED ANTIMICROBIAL OLIGONUCLEOTIDES AND USES THEREOF

(75) Inventors: Yin Chen, Pearland, TX (US); Xin Xing Tan, Manvel, TX (US)

(73) Assignee: Star Biologics, Inc., Houston, TX (US)

( * ) Notice: Subject to any disclaimer, the term of this patent is extended or adjusted under 35 U.S.C. 154(b) by 39 days.

(21) Appl. No.: 11/664,052

(22) PCT Filed: Sep. 28, 2005

(86) PCT No.: PCT/US2005/035263
§ 371 (c)(1),
(2), (4) Date: Mar. 28, 2007

(87) PCT Pub. No.: WO2006/037127
PCT Pub. Date: Apr. 6, 2006

(65) Prior Publication Data
US 2008/0206154 A1    Aug. 28, 2008

Related U.S. Application Data

(60) Provisional application No. 60/613,999, filed on Sep. 28, 2004.

(51) Int. Cl.
C07H 21/04    (2006.01)
C12N 15/11    (2006.01)
C12N 15/00    (2006.01)

(52) U.S. Cl.
USPC ............... 514/44 A; 536/24.5; 435/320.1

(58) Field of Classification Search
None
See application file for complete search history.

(56) References Cited

U.S. PATENT DOCUMENTS 5,512,435 A * 4/1996 Renschler et al. .............. 506/10

FOREIGN PATENT DOCUMENTS

WO    WO 9628472 A1 *  9/1996

\* cited by examiner

*Primary Examiner* — Dana Shin
(74) *Attorney, Agent, or Firm* — Ramey & Browning, PLLC

(57) ABSTRACT

The current invention is directed to oligonucleotide sequences isolated from a sequence designated rbl-1 [SEQ ID NO. 19] that either kill or inhibit growth, or prevent the production of endogenously expressed toxin, of microorganisms. These ssDNA sequences, identified through use of a screening method, appear to act as modulators of essential growth functions which may act at the level of triplex formation, antisense inhibition, or as aptamers that alter gene function. The sequences, referred to as minimum functional regions, or MFRs, are useful inter alia as therapeutic agents for treatment of sepsis and other pathologies caused by microorganisms such as sepsis and/or in which microorganisms are contributory agents.

12 Claims, 5 Drawing Sheets

Figure 1:
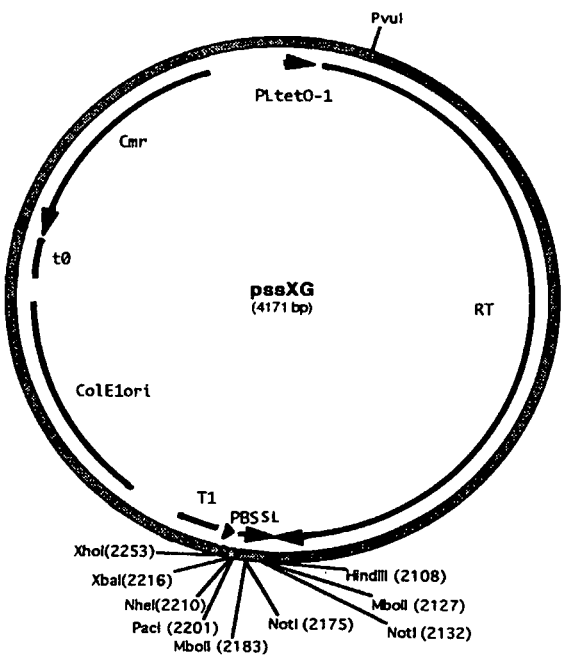
Figure 1:
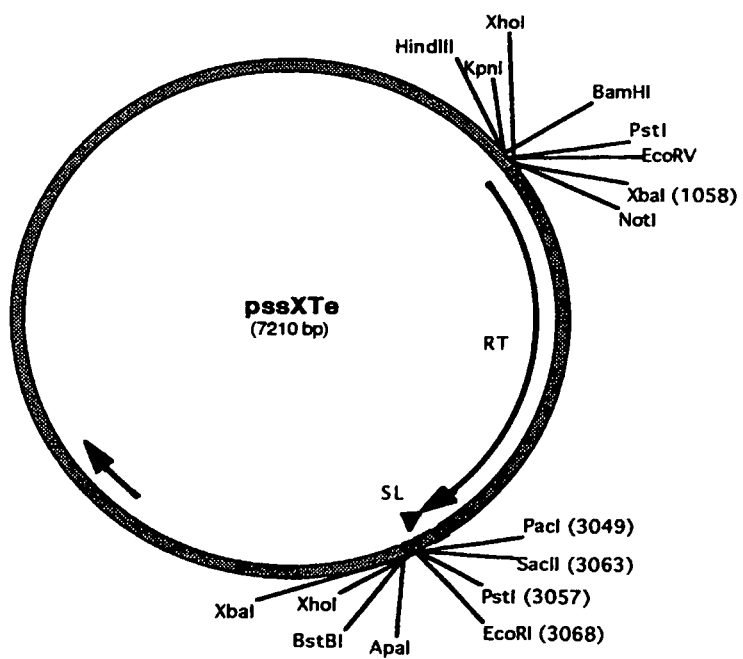

A.

B.

SINGLE-STRANDED ANTIMICROBIAL OLIGONUCLEOTIDES AND USES THEREOF

There is an increasing demand for new antimicrobial therapeutics. Many microbial infections treated with antibiotics are becoming multiply antibiotic resistant and new approaches are needed to combat the pathologies caused by such microbial agents. Although different approaches are being investigated, the present invention involves the use of targeted single-stranded nucleic acids. Oligonucleotide-mediated intervention (OMI) technology provides a powerful tool to alter the activity of any gene of known sequence. The ability to produce single-stranded DNA (ssDNA) of any sequence and length in selected cells enables targeted alteration of gene expression at the genomic level using triplex forming oligonucleotides for targeted gene expression, at the messenger RNA (mRNA) level using antisense and DNA enzyme oligos, and at the protein level using ssDNA as aptamers (Chen, Y. 2002, Expert Opin. Biol. Ther. 2(7) 735-740).

One major parameter determining efficacy of any OMI strategy is target site accessibility. Various approaches to identifying the accessible sites on target mRNAs in relation to antisense and/or DNA enzyme design have been developed. Conventionally, a linear shotgun approach has been used to select antisense ODNs in which several ODNs, targeted to various regions of an mRNA, are synthesized individually and their antisense, DNA enzymatic or other activity (or binding affinity to the target sites) measured. However, only 2-5% of ODNs are usually found to be good antisense reagents.

Computer programs are also used to identify active OMI reagents. For instance, the secondary structure of target RNA is predicted using an RNA folding program such as MFOLD (M. Zuker, 1989, Science, 244, 48-32). Antisense ODNs are designed to bind to regions that are predicted to be free from intramolecular base pairing. However, energy-based prediction methods of RNA structure are largely inadequate for designing antisense reagents and success using this approach has been limited.

Evidence that ribonuclease H(RNase H) is involved in antisense-mediated effects has led to the development of procedures that use this enzyme to identify accessible binding sites in mRNAs in vitro. RNase H is an endoribonuclease that specifically hydrolyzes phosphodiester bonds of RNA in DNA:RNA hybrids. RNase H may be used in combination with a random ODN library comprising a complete set of all possible ODNs of a defined length. For instance, for a length N, there are thus $N^4$ different possible ODNs in the library set such that there are approximately $2.56 \times 10^6$ molecules for a 40-mer ODN. Component ODNs of the library that are complementary to accessible sites on the target RNA produce hybrids with RNA that are identified as RNase H cleavage sites by gel electrophoresis. While many of ODNs in the library set are of no interest, e.g., an ODN such as AAAA . . . AAAA, the library set members are tested to see which, if any, produce a down regulating effect on a specific target mRNA. Controlled gene expression systems such as the tetracycline regulatory system in prokaryotic cells allow selective gene down or up-regulation and thereby supply information on the gene product.

Ji, et al. constructed a library of small staphylococcal DNA fragments (200 to 800 bp) derived by shearing genomic DNA (Ji, et al., 2001, Science, 293:2266-2269). By transforming the library into *Staphylococcus aureus*, random antisense RNA molecules were generated. Using this approach, Ji, et al. identified critical genes that could serve as targets for antibiotic discovery. A similar approach has been used by Forsyth, et al. in *S. aureus* (Forsyth, et al., 2002, Molecular Microbiology, 43:1387-1400). However, this approach can only be used for the identification of essential genes since antisense RNA with the size between 200-800 bp is not useful for therapeutic purposes because of 1) the instability of RNA molecules; 2) the difficulty of synthesizing RNA molecules with the size of 200-800 bp; and 3) the problem of delivering RNA to appropriate cells.

Recent advances in DNA sequencing technology have made it possible to elucidate the entire genome sequences of pathogenic bacteria and therefore provide convenient information for the design of specific genetic tools to combat bacterial and other microbial-based diseases. These tools provide alternatives to traditional anti-microbial treatments and also provide a basis for developing effective therapeutics for non-bacterial infectious agents as well, including viruses, protozoa, fungus, mycoplasma and others.

It is therefore an object of the present invention to provide a method for constructing a randomized library comprising single-stranded expression vectors.

It is also an object of the present invention to utilize this single-stranded expression vector library to identify novel ssDNA sequences or ODNs that when expressed, can alter cell function sufficiently to regulate cell growth.

Another object of the present invention is to provide a method for identifying essential bacterial genes, RNAs and proteins that can serve as targets for controlling cell growth and/or function. Some of these identified targets can then be tools in the development of novel treatments to combat bacterial infections.

Consequently, another object of the present invention is to provide a vector for expression of the newly identified ODN inside a prokaryotic cell which could be either constitutively expressed, or inducible with selective chemical inducers.

It is also an object of the present invention to provide a vector for similar expression of the newly identified ODN inside a eukaryotic host whereby a eukaryotic promoter would regulate expression of the single-stranded ODN; such a promoter may be inducible or constitutively expressed.

An additional object of the present invention is to provide a method for the selective regulation of expression inside a prokaryotic or eukaryotic cell using a universal selectively-inducible expression vector system such as the tetracycline system.

Another object of the present invention is to provide for the identification of novel antibacterial targets identified by practicing the screening methods of the present invention and to utilize phenotypic altering sequences for combating bacterially-originated pathologies.

Another object of the present invention is to provide useful sequences identified as being bacterial growth regulatory sequences to be used as effective active components of therapeutic compositions.

The present invention utilizes a new approach to the need for alternative treatment for antibiotic-resistant bacteria entailing the construction and screening of a selectively-inducible single-stranded DNA (ssDNA) expression library that can be induced to express ssDNA in a prokaryotic host. Disclosed is a method for constructing a ssDNA expression library, as well as a method for screening the library and identifying functionally effective ssDNA molecules capable of regulating bacterial cell growth and/or toxin production.

The method comprises constructing a set of randomly ordered, fixed length oligodeoxynucleotide (ODN) strands and sub-cloning these ODNs into single-stranded expression vectors which are then transformed into cells and induced to express inside the cell. Cells containing the instructions for expression of an individual single-stranded ODN (ss-ODN) are grown into colonies and divided into separate control and experimental sets. The experimental colony is exposed to a chemical inducer specific for induction of the ODN promoter and causes the ODN to be expressed as a single-stranded transcript. The ss-ODN is then capable of interacting with its respective cellular target (DNA, RNA or protein) and can potentially alter cell function upon interaction with an essential cellular component. If the altered cell function creates a desired observable phenotype, the colony exhibiting the altered phenotype can be used as a source of DNA to determine the exact nucleotide sequence of the ss-ODN that produced the phenotype in question.

This method is used to identify ss-ODNs that specifically target essential prokaryotic and eukaryotic cell components which regulate cell function at the level of transcription, translation or protein function. When used in the context of bacterial pathogens, the method of the invention makes it possible to identify new sequences which are utilized in antibacterial therapies to combat growth of all types of pathogenic bacteria.

Once an effective ss-ODN is identified as regulating bacterial growth, the ODN is cloned into a similar single-stranded expression vector designed for a eukaryotic expression system. This second step ODN-eukaryotic expression vector is then used to treat a bacterially challenged person, animal or plant whereby the recipient is exposed to a dose of the ODN-eukaryotic expression vector and upon internalization of the vector by a host cell, the host cell expresses the ODN. Once the ss-ODN is expressed, it can be secreted into the intercellular milieu of the host where it can contact a target bacterial cell, be taken up by the bacterial cell, interact with the regulatory bacterial target, and either inhibit growth of the bacterial cell, or inhibit the production of bacterial toxins.

Referring now to the figures, FIG. 1 is a schematic representation of some of the cloning vectors of the present invention. (A) cloning vector, pssXG, is a modification of mammalian ssDNA expression vector, pssXE, to be a prokaryotic ssDNA expression vector comprising the expression cassette of pssXE, a bacterial tet promoter, and a prokaryotic PBS sequence (TGGTGCGTCCGAG) [SEQ ID NO: 3] that is primed by tRNAVal; (B) cloning vector, pssXTe, comprising the ssDNA expression cassette of pssXE subcloned into the eukaryotic vector, pcDNA4/TO/myc-HisA (Invitrogen) under the control of an inducible eukaryotic tet promoter.

Figure 2:
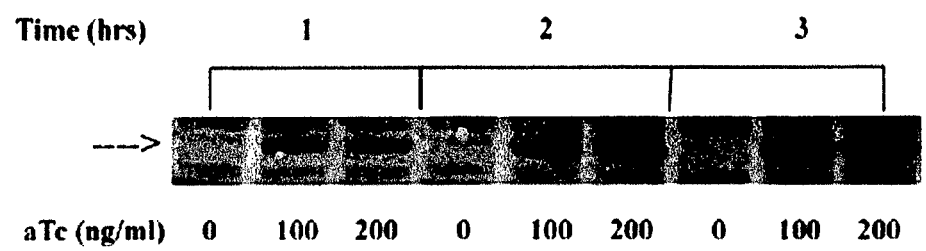

FIG. 2: Expression of reverse transcriptase (RT) induced with aTc in DH5αpro cells. DH5αpro cells carrying the pssXGb, a targeted DNA enzyme vector, were grown in the presence of 0, 100, or 200 ng/ml of aTc for 1 hr (lanes 1-3), 2 hrs (lanes 4-6), or 3 hrs (lanes 7-9). The aTc treated cells were then lysed and the RT expression was determined by western blot analysis.

Figure 3:
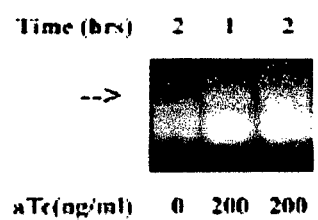

FIG. 3. The activity of the expressed RT in aTc-treated cells was assayed using RT-PCR as described by Chen, et al. Antisense & Nuc Acid Drug Development, 10: 415. RT-PCR products are marked by the arrow.

Figure 4:
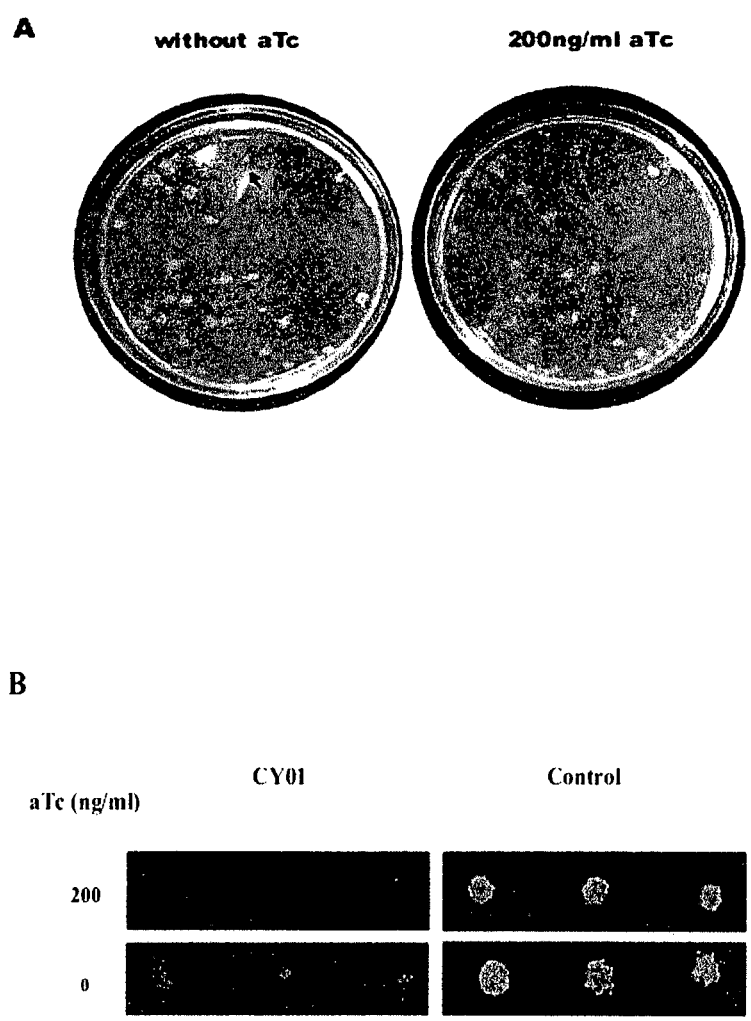

FIG. 4. Screening of a Tet-inducible randomized ssDNA expression library in bacteria. (A) The bacterial transformants were recovered on LB plates containing 34 µg/ml Cm and 50 µg/ml Spec after overnight incubation at 37° C. The LB plates were then replica-plated onto the inducing (200 ng/ml aTc) and non-inducing (without aTc) LB plates. Clone CY01 marked by an arrow, grew normally on non-inducing LB plates but did not grow on the inducing plates were selected for further characterization. (B) Confirmation of lethal phenotype of clone CY01. The phenotype of clone CY01 cells was confirmed by resuspending cells in LB medium and retesting growth on both inducing and non-inducing plates. Control cell contains pssXGb vector only.

Figure 5:
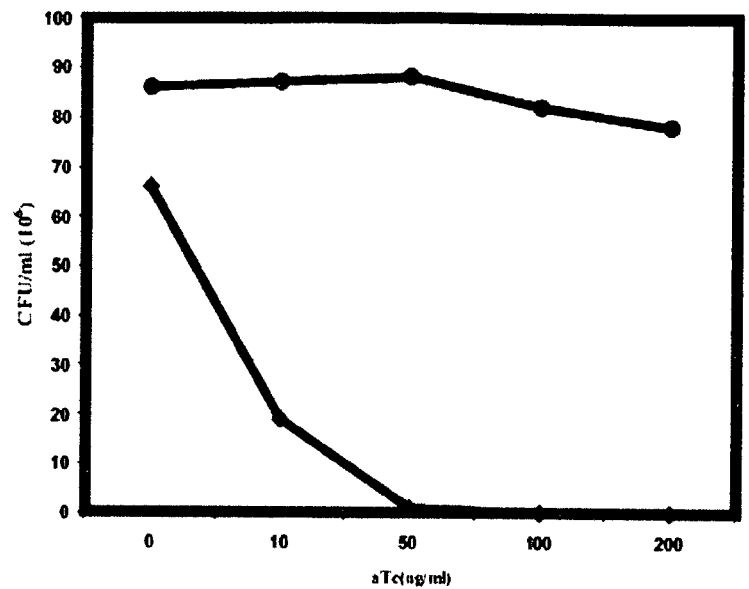
Figure 5:
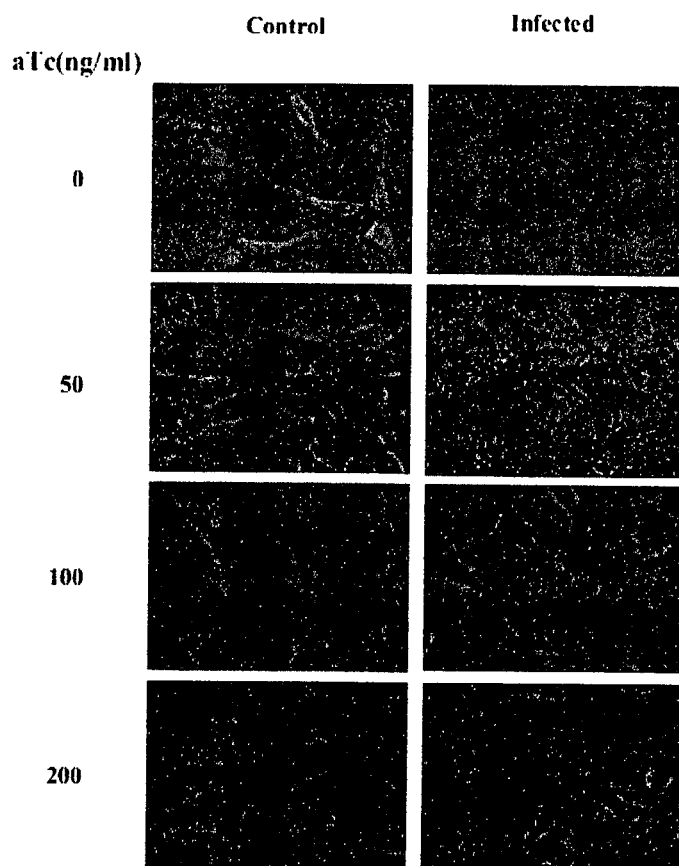

FIG. 5. Inhibition of bacterial cell growth by in vivo generated rbl-1. (A) The inducible expression and inhibition of bacterial cell growth by rbl-1 generated inside the bacterial host cell was determined by measuring the viable cell count. CY01 cells were grown in the presence of 0, 10, 50, 100, or 200 ng/ml of aTc for 1 hr. One ml of sample was removed after 1 hr for measuring viable cell count by diluting the cultures and plating them in triplicate on LB plates containing appropriate antibiotics. Plates were then incubated overnight at 37° C. and the number of colonies enumerated by visual inspection. Bacterial cell growth is shown in squares (CY01 cells) or circles (control CY01c cells). (B) Inhibition of bacterial infection of HeLa cell cultures by expression of rbl-1 inside the eukaryotic HeLa host cell. Left column: HeLa cell cultures transduced and expressing rbl-1, without E. coli infection. Right column: HeLa cell cultures transduced and expressing rbl-1, infected with $10^5$ CFU/ml of CY01 cells. HeLa cell cultures were incubated overnight in the presence of 0, 50, 100 or 200 ng/ml of aTc.

Figure 6:
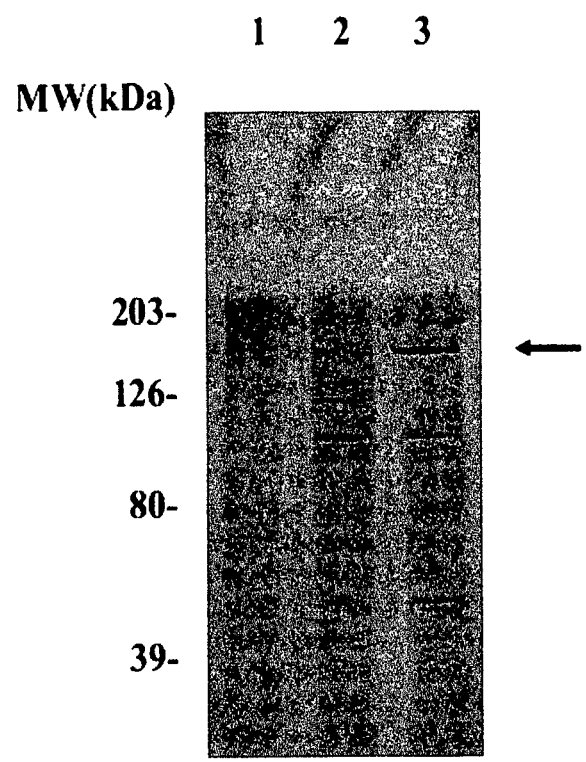

FIG. 6. Identification of rbl-1 binding protein. The rbl-1 binding protein was purified using the avidin-biotin method. DH5αpro cell lysates were incubated with 500 ng biotinylated rbl-1 (lane 3), rbl-1c (lane 2), or none (lane 1) and then streptavidin-agarose beads were added. Proteins that bound to the beads were eluted (50 mM Tris, pH7.5, 100 mM NaCl, 2M KCl, and 4% glycerol) and subjected to SDS-PAGE analysis. Protein was visualized by silver staining using a SilverQuest kit (Invitrogen, Carlsbad, Calif.) according to the manufacturer's instructions. The protein marked with an arrow with a molecular weight of ~160 kDa (lane 3) was excised for sequence identification.

Figure 7:
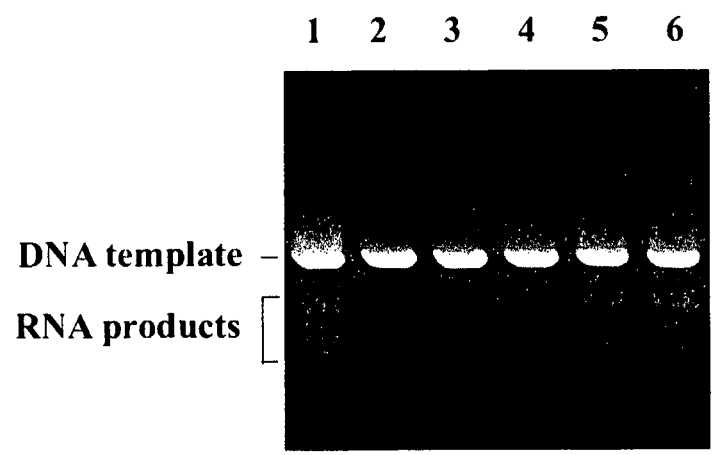

FIG. 7. In vitro inhibition of RNAP activities by rbl-1. RNA products were separated on a 1% agarose gel. Lane 1, control without rbl-1; Lane 2, 0.5 µM rbl-1; Lane 3, 0.25 µM rbl-1; Lane 4, 0.125 µM rbl-1; Lane 5, 0.05 µM rbl-1; and Lane 6, 0.5 µM control rbl-1c.

In more detail, the present invention contemplates the construction of a single-stranded DNA expression library based upon the pssXE single-stranded expression vector system previously described in International Application No. PCT/US03/13593, which is hereby incorporated into this specification in its entirety by this specific reference. In the current invention, a new single-stranded expression vector, pssXG, was constructed which is designed to induce expression of single-stranded oligodeoxyribonucleotide sequences (ss-ODNs) inside a bacterial host cell. Whereas pssXE vector was used to induce ss-ODN expression in eukaryotic host cells, pssXG contains an inducible tetracycline promoter system and a different primer binding site (PBS) to effectuate similar expression of a ss-ODN inside a prokaryotic host cell.

EXAMPLE 1

Construction of an Inducible Prokaryotic ssDNA Expression Vector

PCR amplification of the expression cassette comprising the inverted repeat sequences, cloning sites for the sequence of interest (SOI), a reverse transcriptase specific primer binding site, and the Murine Maloney reverse transcriptase gene was carried out using plasmid pssXE as the PCR template. The DNA primers used in the PCR reaction,

```
5'NheIPvuIATG
                                       [SEQ ID NO: 1]
CTAGCTAGCT AGCGATCGAT GGGACCAATG GGGCAG
and 3'KpnI
                                       [SEQ ID NO: 2]
CGGGGTACCA GTATTCCCTG GTC
```
were synthesized by Integrated DNA Technologies (Coralville, Iowa). The pssXE vector was constructed and described in detail in International Application No. PCT/US03/13593, and the method of PCR amplification was previously described in International Application No. PCT/US04/17331; both applications are herein incorporated by reference in their entirety.

The PCR amplified DNA fragment was double-digested with NheI and KpnI and then subcloned into pssXE vector that was double-digested with the same enzymes. The replacement removes the sequence before the translation starting site (ATG), which is unnecessary for prokaryotic gene expression, while creating a new restriction enzyme site, PvuI. The newly created construct was digested with PvuI and XbaI. The PvuI-XbaI fragment containing all the essential elements for ssDNA production, includes: 1) Mouse Moloney leukemia viral reverse transcriptase (MoMuLV RT) gene coding for a truncated but fully active RT (Tanase & Goff, PNAS, 2000, 85:1777-1781); 2) primer binding site (PBS) along with some flanking regions of the promoter that are essential for the reverse transcription initiation by MoMuLV RT (Shinnick, et al., Nature, 1981, 293:543-548); and 3) stem-loop structure designed for the termination of the reverse transcription reaction all as described in the above-referenced International Application No. PCT/US04/017331 incorporated herein. This DNA fragment was subcloned into the pPROTet.E 233 vector (BD Bioscience, Palo Alto, Calif.) and the newly created construct was designated as pssXG, shown in FIG. 1. However, the sequence of bacteria tRNAPro is different from mammalian tRNAPro, which was designed to bind with the PBS in mammalian cells. Because bacterial tRNAVal can be utilized as primer for RT, a new PBS was designed to replace the PBS used in the vector pssXE that is used for mammalian cells. The sequence of the novel PBS is:

```
        TGGTGCGTCCGAG          [SEQ ID NO: 3]
``` and the created construct was designated as pssXGb (FIG. 1B).

pPROTet.E233 is a tetracycline-inducible bacterial expression vector expressing fusion protein with 6×HN. It utilizes a novel promoter, $P_{Ltet}O1$, which is tightly repressed by the highly specific Tet repressor protein and induced in response to anhydrotetracycline (aTc) which is a type of tetracycline, allowing control of induction over a wide range (anhydrotetracycline is a derivative of tetracycline that acts as a more potent inducer of PROTet.E Systems). The pssXGb vector was transformed into the bacteria strain, DH5αPro (BD Bioscience, Palo Alto, Calif.) in the presence of 34 μg/ml choloramphenicol (Cm) and 50 μg/ml spectinomycin (spec). Spectinomycin is used to select for DH5αPro cells that carry transcription units encoding TetR (Lutz & Bujard, Nucleic Acids Res., 1997, 25:1203-1210). The DH5αPro cells express defined amounts of the Tet repressors. Cell lysates were prepared using B-PER II Bacterial Protein Extraction Reagent (Pierce, Rockford, Ill.) according to the manufacturer's instruction. Using the cell lysates, the expression of reverse transcriptase (RT) was confirmed by RT activity assay using cell lysates according to Silver, et al. (Nucleic Acids Res., 1993, 21:3593-3594) as shown in FIG. 2 and Western blotting using antibody against 6×HN (BD Bioscience, Palo Alto, Calif.) as shown in FIG. 3.

EXAMPLE 2

Construction of an Inducible ssDNA or ODN Expression Library

The library inserts were generated by annealing three ODNs:

```
CY(SacII)-40,
CTCTCACTCC(N)40ACTGTTGAAAGGC      [SEQ ID NO: 4]

CY(SacII)-L,
CGGAGAGTGAGG                       [SEQ ID NO: 5]
and

CY(SacII)-R,
CTTTCAACAGT                        [SEQ ID NO: 6]
``` at the molar ratio of 1:20:20. Here, "N" represents any of the bases A, T, C, or G. There are thus 40-mer sequences randomly synthesized and represented as CY(SacII)-40 ODNs. All the ODNs were mixed and denatured at 95° C. for 3 min and then cooled down slowly to the room temperature over approximately 1 hr. Since CY(SacII)-L complements the left arm of CY(SacII)-40 while CY(SacII)-R complements the right arm of the same ODN, partial double-stranded ODNs are formed by the annealing process. The annealed ODN formed a partial double-stranded DNA and was filled in those remaining single-stranded Ns and blunt ended using the DNA Polymerase I, Large (Klenow) Fragment (New England Biolabs, Beverly, Mass.). The double-stranded DNA was then subcloned into the newly created prokaryotic ssDNA expression vector designated pssXGb, and subsequently transformed into bacterial cells, DH5αPRO using electroporation.

EXAMPLE 3 ssDNA Expression Library Screening

The transformants were recovered on LB plates containing 34 μg/ml Cm and 50 μg/ml Spec after overnight incubation at 37° C. The LB plates were then replica-plated onto inducing (100 ng/ml aTc) and non-inducing (without aTc) LB plates and incubated overnight at 37° C. Colonies that grew normally on LB plates but which either failed to grow or showed growth defects on the inducing plates were selected. The inducer-mediated growth inhibitory effect was confirmed by retesting the selected colonies for cell growth and inducible growth inhibition on inducing and non-inducing plates. Approximately 5,000 transformants were screened. A total of 12 colonies were identified as having inducible growth inhibition when in the presence of aTc.

Plasmids from these colonies were isolated and the inserts sequenced:

```
1. LIB0308:
                                              [SEQ ID NO: 7]
GTAACGCCCA AACCTAAAAA ACCAGAATTA TTGCCCCCGT

2. LIB0309:
                                              [SEQ ID NO: 8]
CGGGCATACA GGTCAAAATC GGGACAAGCG AAGGAATTAA

ACTGTTGAAA GGCCTTTCAA CAGTGTGGAA CTATGATTAT

GCGGATTATC CGGGGCCTCT TTCA
```

3. LIB0902:

[SEQ ID NO: 9]
GAATCAATCA GTAAAAGAAG ATATGCCGAG TTCTGATTAT

GGAGTGAGAG CTCTCACTCC TAAGGCCTCC AGTGAGCGTG

CCAATATGAC TATGTCCTCT ACTGTTGAAA GGCCTTTCAA

CAGTCTATAG ATCTAACGTG CGTTGCGACG CCTCAGGTTAG

AAGG

4. LIB1003:

[SEQ ID NO: 10]
CGCGATCCAC GCTCCCGTGG GTTAAACCGA AGTCGTACCG

ACTGTTGAAA GGCCTTTCAA CAGTTTCCGC ACTGTGTGCA

ATTTTATGAC AAATAGAGTG GGAG

5. LIB1006:

[SEQ ID NO: 11]
GCGCTTGCCA AGGGTAGTAG CCCATAAGTC GAATCAGCTA

CTGTTGAAAG GCCTTTCAAC AGTACTGCAA ATAAAAATGC

AAGAGTCCAA AATATATGGA CCT

6. LIB1102:

[SEQ ID NO: 12]
GTTTGATATG CACACTTACT CTGTCACACT GTTATTTGGC

7. LIB1103:

[SEQ ID NO: 13]
CGCGATCCAC GCTCCCGTGG GTTAAACCGA AGTCGTACCG

ACTGTTGAAA GGCCTTTCAA CAGTTTCCGC ACTGTGTGCA

ATTTTATGAC AAATAGAGTG GGAG

8. LIB1104:

[SEQ ID NO: 14]
TGGGACCGTC TGTACAACCG TTATTAACGC CGGACTGCTT

ACTGTTGAAA GGCCTTTCAA CAGTCCGGAA GAAAGCTGGC

ATCAACTAAG CAAGTCACAA TGAC

9. LIB1304:

[SEQ ID NO: 15]
GCAATACCCT ACCGACAGCG CTTAAAGTAT TATCGTCTTC

ACTGTTGAAA GGCCTTTCAA CAGTGATCAT CTATGCGTTC

TGACGAGTGC TTGCGTCTTC CCGG

10. LIB1305:

[SEQ ID NO: 16]
GCGGAAGTAA TGGGTGGACA AGACGTAACA GCGCGCT

11. LIB1406:

[SEQ ID NO: 17]
ACAGCAGTCT GCAAGTAAGA TGTGTTGATC ATAAAAAGT

ACTGTTGAAA GGCCTTTCAA CAGTGCAAAT GCCATTGGCG

AGCGGACTTT GTGGTACTAG CTATC.

12 LIB CY01 (40-mer rbl-1):

[SEQ ID NO: 18]
TTTGATGACC TTTGCTGACC ATACAATTGC GATATCGTGG

A lethal phenotype is induced in the presence of aTc in clone CY01 while the remaining 11 colonies were inducibly growth-defective. The lethal phenotype was further confirmed by resuspending cells in LB medium and retesting growth on both inducing and non-inducing plates (FIG. 4). The isolated plasmid was designated AS080103 comprising a 61 nucleotide rbl-1 insert, CYGX080103, having the sequence:

[SEQ ID NO: 19]
CTTTCAACAG TTTTGATGAC CTTTGCTGAC CATACAATTG

CGATATCGTG GGGAGTGAGA G which in addition to the original library oligomers, SEQ ID NOS. 4, 5 and 6, contains the randomly synthesized 40-mer ODN designated as rbl-1, SEQ ID NO: 18, above.

A control vector, CY01c, comprising the same vector but containing a sequence encoding for a sequence complementary to rbl-1, designated rbl-1c, was used to validate regulation by the rbl-1 sequence. A double-stranded insert of the control rbl-1c was generated by annealing two complementary synthesized ODNs (Integrated DNA Technologies, Coraville, Iowa), having the final sequence:

[SEQ ID NO: 20]
TAACTTTCAA CAGTTTTGAT GACCTTTGCT GACCATACAA

TTGCGATATC GTGGGGAGTG AGAGT

EXAMPLE 4

Inhibition of Bacterial Cell Growth by In Vivo Generated rbl-1

To further characterize the antibacterial effect of rbl-1, the aTc dose response of cell growth inhibition by rbl-1 generated in vivo was investigated. CY01 cells were grown in the presence of various concentrations of aTc (0, 10, 50, 100, or 200 ng/ml) for 1 hr and viable cells were enumerated. CY01c, constructed to generate a complementary sequence of rbl-1, rbl-1c, was used as a control. FIG. 5 shows that cell growth inhibition by rbl-1 is aTc-concentration dependent. However, there is no significant inhibition of cell growth when rbl-1c is generated in control CY01c cells, indicating that the inhibition is rbl-1 sequence specific and not caused by aTc.

To examine the antibacterial potential of RBL-1 in the presence of eukaryotic cells, which is more relevant for in vivo application, CY01 cell growth in HeLa cell culture medium was tested. HeLa cell cultures were infected with $10^5$ CFU/ml of CY01 cells in the presence of various concentrations of aTc (0, 50, 100, or 200 ng/ml). As shown in FIG. 5, sufficient copies of rbl-1 were generated to fully cure the HeLa culture of the infection when 100 ng/ml of aTc or higher was used.

EXAMPLE 5

Identification of rbl-1 Targeting Molecule(s)

Through randomized ssDNA expression library screening, an antibacterial ODN, designated rbl-1 was identified. To understand the mechanism of rbl-1 antibacterial activity, a gene sequence homology analysis was performed. Smaller regions of the RBL-1 sequence were identified as having complementarity to known GenBank sequences, suggesting potential targets for antisense inactivation by the rbl-1 ODN through potential hybridization to the identified target mRNAs in vivo. Some of these smaller ODNs having ten or more base pair homology, are listed in Table 1.

TABLE 1

Sub-sequences of rbl-1 complementary to known target mRNAs.

| Experimental ID | Sub-sequence | Potential Target | Genbank Identifier | SEQ ID NO |
|---|---|---|---|---|
| CYGX 08010301 | CCTTTGCTGA CCATAC | btuE | NP_416225.1 | 21 |
| CYGX 08010302 | GACCTTTGCT GACCA | CaiB | NP_414580.1 | 22 |
| CYGX 08010303 | ACAGTTTTGA TGAC | ydgD | NP_418152.1 | 23 |
| CYGX 08010304 | ACAATTGCGA TAT | ygcQ | NP_417249.2 | 24 |
| CYGX 08010305 | GACCTTTGCT GAC | ftsH | NP_417645.1 | 25 |
| CYGX 08010306 | TCAACAGTTTTGATGAC | ppiB | NP_415058.1 | 26 |
| CYGX 08010307 | ATGACCTTTG CTG | yihl | NP_418308.1 | 27 |
| CYGX 08010308 | CAGTTTTGAT GA | zntA | NP_417926.1 | 28 |
| CYGX 08010309 | ACCTTTGCTG AC | yicI | NP_418116.1 | 29 |
| CYGX 08010310 | TTGCTGACCA TA | fhuA | NP_414692.1 | 30 |
| CYGX 08010311 | TGACCTTTGC TG | rplD | NP_417778.1 | 31 |
| CYGX 08010312 | GTTTTGATGA CC | ilvB | NP_418127.1 | 32 |
| CYGX 08010313 | GCGATATCGT GG | lepB | NP_417063.1 | 33 |
| CYGX 08010314 | TTGATGACCT TT | aroK | NP_417849.1 | 34 |
| CYGX 08010315 | TGGGGAGTGA G | mfd | NP_415632.1 | 35 |
| CYGX 08010316 | TTGCTGACCA T | rlpA | NP_415166.1 | 36 |
| CYGX 08010317 | TTTTGATGAC C | accA | NP_414727.1 | 37 |
| CYGX 08010318 | TGATGACCTT T | pgpA | NP_414952.1 | 38 |

Expression vectors were constructed to generate partial rbl-1 sequences against the *E. coli* genes, btuE, and CaiB in bacterial cells but none of these showed any inhibitory activities at the genetic level, suggesting that rbl-1 may instead exhibit inhibitory effects by targeting critical proteins or other structural molecules.

To identify potential rbl-1 binding protein(s), an affinity purification procedure was developed. DH5α cell lysates were incubated with biotinylated rbl-1 and then immobilized onto streptavidin agarose beads. The bead complexes were washed and bound proteins were eluted and fractionated by SDS-PAGE. Cell lysates incubated with rbl-1c or agarose beads alone were used as controls. As shown in FIG. 6, the affinity profile of rbl-1 binding proteins was different from both controls, and a protein with molecular weight of ~160 kDa (marked by an arrow) specifically binds rbl-1. This protein band was excised and analyzed by Nano-HPLC/electrospray mass spectrometry. Table 2 shows that 34 of the identified peptides localize to 29 regions of bacterial RNAP in the GenBank database, indicating RNA polymerase is a potential rbl-1 binding protein.

TABLE 2

Peptide sequences of rbl-1 binding protein, RNAP

| SEQUENCE | Region of RNAP | SEQ ID NO |
|---|---|---|
| Lys Ile Thr Gln Gly Asp Asp Leu Ala Pro Gly Val Leu Lys | 1046-1059 | 39 |
| Asp Leu Ser Glu Glu Leu Gln Ile Leu Glu Ala Gly Leu Phe Ser Arg | 970-985 | 40 |
| Ala Val Ala Val Asp Ser Gly Val Thr Ala Val Ala Lys | 718-730 | 41 |

TABLE 2-continued

Peptide sequences of rbl-1 binding protein, RNAP

| SEQUENCE | Region of RNAP | SEQ ID NO |
|---|---|---|
| Val Ala Phe Met Pro Trp Asn Gly Tyr Asn Phe Glu Asp Ser Ile Leu Val Ser Glu Arg | 813-832 | 42 |
| Ile Thr Gln Gly Asp Asp Leu Ala Pro Gly Val Leu Lys | 1047-1059 | 43 |
| Val Asp Leu Ser Thr Phe Ser Asp Glu Glu Val Met Arg | 1170-1182 | 44 |
| Leu Gly Glu Pro Val Phe Asp Val Gln Glu Cys Gln Ile Arg | 86-99 | 45 |
| Ala Leu Glu Ile Glu Glu Met Gln Leu Lys | 956-965 | 46 |
| Ser Pro Gly Val Phe Phe Asp Ser Asp Lys | 163-172 | 47 |
| Ala Leu Asn Tyr Thr Thr Glu Gln Ile Leu Asp Leu Phe Phe Glu Lys | 223-238 | 48 |
| Arg Ile Glu Thr Leu Phe Thr Asn Asp His Gly Pro Tyr Ile Ser Glu Thr Leu Arg | 343-363 | 49 |
| Glu Ala Ala Glu Ser Leu Phe Glu Asn Leu Phe Phe Ser Glu Asp Arg | 390-405 | 50 |
| Glu Phe Phe Gly Ser Ser Gln Leu Ser Gln Phe Met Asp Gln Asn Asn Pro Leu Ser Glu Ile Thr His Lys | 515-538 | 51 |
| Trp Leu Glu Leu Gly Leu Thr Asp Glu Glu Lys | 1008-1018 | 52 |
| Ile Glu Thr Leu Phe Thr Asn Asp Leu Asp His Gly Pro Tyr Ile Ser Glu Thr Leu Arg | 344-363 | 53 |
| Glu Ala Ala Glu Ser Leu Phe Glu Asn Leu Phe Phe Ser Glu Asp Arg Tyr Asp Leu Ser Ala Val Gly Arg | 390-413 | 54 |
| Asp Gln Val Asp Tyr Met Asp Val Ser Ter Gln Gln Val Val Ser Val Gly Ala Ser Leu Ile Pro Phe Leu Glu His Asp Asp Ala Asn Arg | 659-689 | 55 |
| Arg Gly Gly Val Val Gln Tyr Val Asp Ala Ser Arg | 731-742 | 56 |
| Gly Met Pro Ile Ala Thr Pro Val Phe Asp Gly Ala Lys | 1190-1202 | 57 |
| Ser Val Phe Pro Ile Gln Ser Tyr Ser Gly Asn Ser Glu Leu Gln Tyr Val Ser Tyr Arg | 66-85 | 58 |
| Glu Glu Ile Glu Gly Ser Gly Ile Leu Ser Lys Asp Asp Ile Ile Asp Val Met Lys | 423-441 | 59 |
| Met Asn Ile Gly Gln Ile Leu Glu Thr His Leu Gly Met Ala Ala Lys | 1118-1133 | 60 |
| Val Pro Asn Gly Val Ser Gly Thr Val Ile Asp Val Gln Val Phe Thr Arg | 931-947 | 61 |
| Leu Asp Glu Ser Gly Ile Val Tyr Ile Gly Ala Glu Val Thr Gly Gly Asp Ile Leu Val Gly Lys | 876-897 | 62 |
| Ser Lys Gly Glu Ser Ser Leu Phe Ser Arg | 549-658 | 63 |
| Ile Asn Pro Ile Glu Asp Met Pro Tyr Asp Glu Asn Gly Thr Pro Val Asp Ile Val Leu Asn Pro Leu Gly Val Pro Ser Arg | 1090-1117 | 64 |
| Leu Asn His Leu Val Asp Asp Lys | 1246-1253 | 65 |
| Val Asp His Pro Thr His Tyr Gly Arg | 560-568 | 66 |
| Val Asn Glu Asp Glu Met Tyr Pro Gly Glu Ala Gly Ile Asp Ile Tyr Asn Leu Thr Lys | 747-766 | 67 |
| Gly Glu Thr Gln Leu Thr Pro Glu Glu Lys | 902-911 | 68 |
| Met Met Arg Pro Gly Glu Pro Pro Thr Arg | 380-389 | 69 |
| Leu Pro Ala Thr Ile Ile Leu Arg | 215-222 | 70 |

EXAMPLE 6

In Vitro Inhibition of RNA Polymerase Activity by rbl-1

To test whether rbl-1 or the minimal functional regions directly inhibit *E. coli* RNA polymerase activity, an in vitro transcription assay was done to assess the inhibitory effect of the 40-mer rbl-1 ODN on the polymerase itself. FIG. 7 shows the results of an in vitro RNA transcription assay. At the lower concentration of 0.05 uM, RNA products were observable indicating that this concentration failed to fully inhibit in vitro RNA polymerase activity; however, at concentrations of 0.125, 0.25, and 0.5 μM the rbl-1 ODN significantly inhibited activity.

EXAMPLE 7

Identification of Minimal Functional Region (MFR) of rbl-1

To better identify the active inhibitory portion of the rbl-1 ODN, a series of truncated rbl-1 oligonucleotides were synthesized (Table 3), and their inhibitory activities were assessed using in vitro RNA polymerase activity assays. Truncated rbl-1 oligos with 3' deletions of various lengths were synthesized first. At the concentration of 5 μM, only rbl-1(1-35) and rbl-1(1-30) showed inhibitory activity, whereas rbl-1(1-25), rbl-1(1-20), and rbl-1(1-15) did not inhibit activity (Table 3). The effect of 5' deletions was then investigated. Except for rbl-1(26-40), all 5' truncated rbl-1 oligos, including rbl-1(6-40), rbl-1 (11-40), rbl-1 (16-40) and rbl-1(21-40), were active (Table 3). On the basis of these in vitro assays, the minimal functional region of rbl-1 comprises an oligo ranging between 7 and 40 nucleotides in length, and preferably between 7 and 15 oligos, including the region spanning and including nucleotides 25-31 and preferably nucleotides 21-32.

TABLE 3

Identification of the minimal functional region (MFR) of RBL-1

| ODN | Fragment Sequence | Activity |
|---|---|---|
| | TTTGATGACC TTTGCTGACC ATACAATTGC GATATCGTGG | |
| rbl-1 | | ++++ |
| rbl-1 (01-35) | | ++++ |
| rbl-1 (01-30) | | ++++ |
| rbl-1 (01-25) | | - |
| rbl-1 (01-20) | | - |
| rbl-1 (01-15) | | - |
| rbl-1 (06-40) | | ++++ |
| rbl-1 (11-40) | | ++++ |
| rbl-1 (16-40) | | ++++ |
| rbl-1 (21-40) | | ++++ |
| rbl-1 (26-40) | | - |
| rbl-1 (21-30) | | - |
| rbl-1 (21-32) | | + |
| rbl-1 (21-34) | | ++ |
| rbl-1 (21-36) | | ++++ |
| rbl-1 (21-38) | | ++++ |
| rbl-1c | | - |

ODN inhibitory activities against RNA polymerase were determined by visualization of band intensity in gel. ++++, 100%; +++, ~75%; ++, ~50%; +, ~25%; -, non-detectable.

TABLE 4 rbl-1 Fragment Sequences

| (rbl-1) | TTTGATGACC TTTGCTGACC ATACAATTGC GATATCGTGG | [SEQ ID NO: 18] |
|---|---|---|
| (01-35) | TTTGATGACC TTTGCTGACC ATACAATTGC GATAT | [SEQ ID NO: 71] |
| (01-30) | TTTGATGACC TTTGCTGACC ATACAATTGC | [SEQ ID NO: 72] |
| (01-25) | TTTGATGACC TTTGCTGACC ATACA | [SEQ ID NO: 73] |
| (01-20) | TTTGATGACC TTTGCTGACC | [SEQ ID NO: 74] |
| (01-15) | TTTGATGACC TTTGC | [SEQ ID NO: 75] |
| (06-40) | TGACCTTTGC TGACCATACA ATTGCGATAT CGTGG | [SEQ ID NO: 76] |
| (11-40) | TTTGCTGACC ATACAATTGC GATATCGTGG | [SEQ ID NO: 77] |
| (16-40) | TGACCATACA ATTGCGATAT CGTGG | [SEQ ID NO: 78] |
| (21-40) | ATACAATTGC GATATCGTGG | [SEQ ID NO: 79] |
| (26-40) | ATTGCGATAT CGTGG | [SEQ ID NO: 80] |
| (21-30) | ATACAATTGC | [SEQ ID NO: 81] |
| (21-32) | ATACAATTGC GA | [SEQ ID NO: 82] |
| (21-34) | ATACAATTGC GATA | [SEQ ID NO: 83] |
| (21-36) | ATACAATTGC GATATC | [SEQ ID NO: 84] |
| (21-38) | ATACAATTGC GATATCGT | [SEQ ID NO: 85] |

One skilled in the art will appreciate that although we have demonstrated that rbl-1 and its active minimal functional regions clearly bind to and inhibit activity of bacterial RNA polymerase in vitro, one should not presume that these ODNs exert their growth inhibitory effect of the bacterial cell solely by this mechanism alone. It is likely that inside a cell, rbl-1 and its mfrs can also interact with additional cellular components which may include other essential nucleic acids, proteins, peptides, carbohydrates, or other essential growth regulating compounds that may contribute to the growth inhibitory phenotype described herein.

One skilled in the art will also recognize from this disclosure that sequences having substantial homology to the sequences herein disclosed would likely be functional equivalents and are therefore considered as part of the current invention. A sequence is considered homologous in this context if the sequence either comprises a 70% or greater basefor-base nucleotide match, or has a similar functional activity for the assays herein disclosed and related growth regulatory activities, including but not limited to growth inhibition and inhibition of in vitro RNA polymerase activity.

EXAMPLE 8

Construction of the pssXTe Eukaryotic ssDNA Expression Vector

To construct a eukaryotic ssDNA expression cassette from the pssXE vector, an XhoI site was created before the protein translation site, ATG. A DNA fragment was generated by PCR amplification from the pssXE template using the primers

```
5'NheIXhoIXbaIATG,
                               [SEQ ID NO: 1]
CTAGCTAGCT AGCGATCGAT GGGACCAATG GGGCAG
and 3'KpnI,
                               [SEQ ID NO: 2]
CGGGGTACCAGTATTCCCTGGTC'
```

The amplified PCR DNA fragment was then digested with NheI and KpnI and subcloned into the NheI and KpnI double-digested pssXE vector. The resulting intermediate plasmid was designated as pssXE(NXX). To subclone the ssDNA expression cassette into pcDNA4/TO/myc-HisA (purchased from Invitrogen), the EcoRI site of this vector had to be destroyed. The pcDNA4/TO/myc-HisA vector was initially digested with BamBI and EcoRI, then a double-stranded oligo comprising the sequences

```
5'BamHIEcoRI(m),
GATCCACTAG TCCAGTGTGG TGT      [SEQ ID NO: 86]
and

3'-BamHIEcoRI(m),
GAATTACACC ACACTGGACT AGTG     [SEQ ID NO: 87]
``` was subcloned into the digested vector.

A ssDNA expression cassette was isolated from pssXE (NXX) following XhoI digestion and subcloned into the XhoI site of the modified pcDNA4/TO/myc-HisA vector as described above. The correct orientation of the ssDNA expression cassette was confirmed by DNA sequencing and the newly created vector was designated pssXTe. The pssXTe vector is a ssDNA expression vector that is inducible with aTc in eukaryotic cells and thus enables the controlled inducible expression of an ODN in a eukaryotic cell. The ODN may be either directed at a eukaryotic target, or a prokaryotic target that may be produced in a eukaryotic host cell of an animal and secreted into the bloodstream or other bodily fluid depending on the tissue targeted for expression, whereby an antimicrobial ODN may come in contact with the pathogen and may effectuate killing or inactivating the cell, or it may act to neutralize a secrreted bacterial toxin that is in the bloodstream.

The present invention relates to a new strategy for combating bacterial and fungal pathogens, wherein selected ODNs and the expression plasmid used to produce them are used as therapeutic agents. One such pathogenic condition that is treated successfully utilizing the ODNs and expression plasmids of the present invention is sepsis. Examples of sepsis-causing microorganisms that can be treated in accordance with the present invention include, but are not limited to, those that cause infections in the lung, abdomen, bloodstream, skin, soft tissue, infections associated with intravascular devices, and respiratory infections. Examples of other pathogenic microorganisms that can be treated in accordance with the present invention include, but are not limited to, Gram-negative bacteria such as *Bacteroides, Fusobacterium, Escherichia, Klebsiella, Salmonella, Shigella, Proteus, Pseudomonas, Vibrio, Legionella, Haemophilus, Bordetella, Brucella, Campylobacter, Neisseria, Branhamella*; Gram-positive bacteria such as *Streptococcus, Staphylococcus, Peptococcus, Bacillus, Listeria, Clostridium, Propionebacteria*; organisms that stain poorly or not at all with Gram's stain such as *Mycobacteria, Treponema, Leptospira, Borrelia, Mycoplasma, Clamydia, Rickettsia* and *Coxiella*; and fungi such as *Candida, Aspergillosis, Blastomycosis, Coccidioidomycosis, Cryptococcosis, Histoplasmosis, Paracoccidiomycosis, Sporotrichosis, Zygomycosis*.

When utilized in a method of treatment of a pathology in which a microorganism is a causative or contributory agent, MFRs of rbl-1 may be utilized in any of several ways depending upon the particular pathology, the causative or contributory agent, the type of affected individual (human vs. animal), the condition of the affected individual, and many other factors that will be apparent to those skilled in the art from the foregoing disclosure. MFRs of rbl-1 may, for instance, be administered to an infected open wound by suspending multiple copies of a plasmid comprising the MFR in an acceptable diluent or carrier and spraying or bathing the wound. In the case of, for instance, a bacterial or fungal infection of the lungs, the suspension may be administered as an aerosol for inhalation by the affected individual. Regardless of whether the MFR is administered as a suspended sequence, a suspended plasmid or other expression vector, or in the many other ways known in the art, an adjuvant may also be utilized to advantage, and other therapeutic agents (such as an antibacterial or antifungal) may be included in the diluent or carrier.

Those skilled in the art will also recognize that the MFR may be conjugated to a peptide wherein the peptide is a peptide selected for its ability to functionally alter the growth or function of a microbial cell. For instance, bacterial targeting peptides such as KFFKFFKFFK [SEQ ID NO. 88], FFK-FFKFFK [SEQ ID NO. 89], LLKLLLKLLLK [SEQ ID NO. 90], KKFKVKFVVKKC [SEQ ID NO. 91], FFRFFRFFR [SEQ ID NO. 92], LLKLLKLLK [SEQ ID NO. 93] or other such microbial targeting peptides, homologs or derivatives thereof which may comprise naturally occurring or modified amino acids (Brogden, Nature Online Reviews, doi:10.1038/nrmicro1098, Feb. 10, 2005; Kaihatsu, et al., Biochem 43: 14340, 2004; Varra and Porro, Antimicrobial Agents and Chemo 40: 1801, 1996; U.S. Pat. Nos. 5,652,211, 5,864,010, and 6,548,651; and WO 2004/024757) may be utilized to advantage in a conjugate for treatment of pathologies in which a microorganism is a causative or contributory agent.

Those skilled in the art will recognize from this disclosure that changes can be made to the component parts and/or steps of the present invention without changing the manner in which those components/steps function to achieve their intended result. All such changes, and others that will be clear to those skilled in the art from this description of the invention, are intended to fall within the scope of the following claims.

SEQUENCE LISTING

<160> NUMBER OF SEQ ID NOS: 87

<210> SEQ ID NO 1
<211> LENGTH: 36
<212> TYPE: DNA
<213> ORGANISM: artificial sequence
<220> FEATURE:
<223> OTHER INFORMATION: DNA primer 5'NheIPvuIATG

<400> SEQUENCE: 1
ctagctagct agcgatcgat gggaccaatg gggcag                              36

<210> SEQ ID NO 2
<211> LENGTH: 23
<212> TYPE: DNA
<213> ORGANISM: artificial sequence
<220> FEATURE:
<223> OTHER INFORMATION: DNA primer 3'KpnI

<400> SEQUENCE: 2
cggggtacca gtattccctg gtc                                            23

<210> SEQ ID NO 3
<211> LENGTH: 13
<212> TYPE: DNA
<213> ORGANISM: artificial sequence
<220> FEATURE:
<223> OTHER INFORMATION: noval primer binding site (PBS) designed to
      replace the PBS used in the vector pssXE that is used for
      mammalian cells
<220> FEATURE:
<221> NAME/KEY: primer_bind
<222> LOCATION: (1)..(13)
<223> OTHER INFORMATION: noval Primer Binding Site

<400> SEQUENCE: 3
tggtgcgtcc gag                                                       13

<210> SEQ ID NO 4
<211> LENGTH: 63
<212> TYPE: DNA
<213> ORGANISM: artificial sequence
<220> FEATURE:
<223> OTHER INFORMATION: CY(SacII)-40, one of the three ODNs used to
      generate library inserts for an inducible ssDNA or ODN expression
      library
<220> FEATURE:
<221> NAME/KEY: misc_feature
<222> LOCATION: (11)..(50)
<223> OTHER INFORMATION: N can be any one of the bases A, T, G, or C

<400> SEQUENCE: 4
ctctcactcc nnnnnnnnnn nnnnnnnnnn nnnnnnnnnn nnnnnnnnnn actgttgaaa    60
ggc                                                                  63

<210> SEQ ID NO 5
<211> LENGTH: 12
<212> TYPE: DNA
<213> ORGANISM: artificial sequence
<220> FEATURE:
<223> OTHER INFORMATION: CY(SacII)-L, one of the three ODNs used to
      generate library inserts for an inducible ssDNA or ODN expression
      library

<400> SEQUENCE: 5
cggagagtga gg                                                        12

```
<210> SEQ ID NO 6
<211> LENGTH: 11
<212> TYPE: DNA
<213> ORGANISM: artificial sequence
<220> FEATURE:
<223> OTHER INFORMATION: CY(SacII)-R, one of the three ODNs used to
      generate library inserts for an inducible ssDNA or ODN expression
      library

<400> SEQUENCE: 6
ctttcaacag t                                                          11

<210> SEQ ID NO 7
<211> LENGTH: 40
<212> TYPE: DNA
<213> ORGANISM: artificial sequence
<220> FEATURE:
<223> OTHER INFORMATION: ssDNA expression library insert LIB0308

<400> SEQUENCE: 7
gtaacgccca aacctaaaaa accagaatta ttgcccccgt                            40

<210> SEQ ID NO 8
<211> LENGTH: 104
<212> TYPE: DNA
<213> ORGANISM: artificial sequence
<220> FEATURE:
<223> OTHER INFORMATION: ssDNA expression library insert LIB0309

<400> SEQUENCE: 8
cgggcataca ggtcaaaatc gggacaagcg aaggaattaa actgttgaaa ggcctttcaa      60
cagtgtggaa ctatgattat gcggattatc cggggcctct ttca                     104

<210> SEQ ID NO 9
<211> LENGTH: 165
<212> TYPE: DNA
<213> ORGANISM: artificial sequence
<220> FEATURE:
<223> OTHER INFORMATION: ssDNA expression library insert LIB0902

<400> SEQUENCE: 9
gaatcaatca gtaaaagaag atatgccgag ttctgattat ggagtgagag ctctcactcc      60
taaggcctcc agtgagcgtg ccaatatgac tatgtcctct actgttgaaa ggcctttcaa    120
cagtctatag atctaacgtg cgttgcgacg cctcaggtta gaagg                    165

<210> SEQ ID NO 10
<211> LENGTH: 104
<212> TYPE: DNA
<213> ORGANISM: artificial sequence
<220> FEATURE:
<223> OTHER INFORMATION: ssDNA expression library insert LIB1003

<400> SEQUENCE: 10
cgcgatccac gctcccgtgg gttaaaccga agtcgtaccg actgttgaaa ggcctttcaa      60
cagtttccgc actgtgtgca attttatgac aaatagagtg ggag                     104

<210> SEQ ID NO 11
<211> LENGTH: 103
<212> TYPE: DNA
<213> ORGANISM: artificial sequence
<220> FEATURE:
<223> OTHER INFORMATION: ssDNA expression library insert LIB1006

<400> SEQUENCE: 11
```

```
gcgcttgcca agggtagtag cccataagtc gaatcagcta ctgttgaaag gcctttcaac      60
agtactgcaa ataaaaatgc aagagtccaa aatatatgga cct                       103
```

<210> SEQ ID NO 12
<211> LENGTH: 40
<212> TYPE: DNA
<213> ORGANISM: artificial sequence
<220> FEATURE:
<223> OTHER INFORMATION: ssDNA expression library insert LIB1006

<400> SEQUENCE: 12

```
gtttgatatg cacacttact ctgtcacact gttatttggc                            40
```

<210> SEQ ID NO 13
<211> LENGTH: 104
<212> TYPE: DNA
<213> ORGANISM: artificial sequence
<220> FEATURE:
<223> OTHER INFORMATION: ssDNA expression library insert LIB1103

<400> SEQUENCE: 13

```
cgcgatccac gctcccgtgg gttaaaccga agtcgtaccg actgttgaaa ggcctttcaa      60
cagtttccgc actgtgtgca attttatgac aaatagagtg ggag                      104
```

<210> SEQ ID NO 14
<211> LENGTH: 104
<212> TYPE: DNA
<213> ORGANISM: artificial sequence
<220> FEATURE:
<223> OTHER INFORMATION: ssDNA expression library insert LIB1104

<400> SEQUENCE: 14

```
tgggaccgtc tgtacaaccg ttattaacgc cggactgctt actgttgaaa ggcctttcaa      60
cagtccggaa gaaagctggc atcaactaag caagtcacaa tgac                      104
```

<210> SEQ ID NO 15
<211> LENGTH: 104
<212> TYPE: DNA
<213> ORGANISM: artificial sequence
<220> FEATURE:
<223> OTHER INFORMATION: ssDNA expression library insert LIB1304

<400> SEQUENCE: 15

```
gcaataccct accgacagcg cttaaagtat tatcgtcttc actgttgaaa ggcctttcaa      60
cagtgatcat ctatgcgttc tgacgagtgc ttgcgtcttc ccgg                      104
```

<210> SEQ ID NO 16
<211> LENGTH: 37
<212> TYPE: DNA
<213> ORGANISM: artificial sequence
<220> FEATURE:
<223> OTHER INFORMATION: ssDNA expression library insert LIB1305

<400> SEQUENCE: 16

```
gcggaagtaa tgggtggaca agacgtaaca gcgcgct                               37
```

<210> SEQ ID NO 17
<211> LENGTH: 105
<212> TYPE: DNA
<213> ORGANISM: artificial sequence
<220> FEATURE:
<223> OTHER INFORMATION: ssDNA expression library insert LIB1406

<400> SEQUENCE: 17
acagcagtct gcaagtaaga tgtgttgatc ataaaaaagt actgttgaaa ggcctttcaa    60
cagtgcaaat gccattggcg agcggacttt gtggtactag ctatc    105

<210> SEQ ID NO 18
<211> LENGTH: 40
<212> TYPE: DNA
<213> ORGANISM: artificial sequence
<220> FEATURE:
<223> OTHER INFORMATION: ssDNA expression library insert LIB CY01
      (40-mer rbl-1)

<400> SEQUENCE: 18
tttgatgacc tttgctgacc atacaattgc gatatcgtgg    40

<210> SEQ ID NO 19
<211> LENGTH: 61
<212> TYPE: DNA
<213> ORGANISM: artificial sequence
<220> FEATURE:
<223> OTHER INFORMATION: rbl-1 insert CYGX080103

<400> SEQUENCE: 19
ctttcaacag ttttgatgac ctttgctgac catacaattg cgatatcgtg gggagtgaga    60
g    61

<210> SEQ ID NO 20
<211> LENGTH: 65
<212> TYPE: DNA
<213> ORGANISM: artificial sequence
<220> FEATURE:
<223> OTHER INFORMATION: double-stranded insert of the control rbl-1c

<400> SEQUENCE: 20
taactttcaa cagttttgat gacctttgct gaccatacaa ttgcgatatc gtggggagtg    60
agagt    65

<210> SEQ ID NO 21
<211> LENGTH: 16
<212> TYPE: DNA
<213> ORGANISM: artificial sequence
<220> FEATURE:
<223> OTHER INFORMATION: Sub-sequences of rbl-1 complementary to known
      target mRNAs (CYGX 08010301)
<220> FEATURE:
<221> NAME/KEY: misc_binding
<222> LOCATION: (1)..(16)
<223> OTHER INFORMATION: Potential mRNA target: btuE corresponding to
      GenBank ID: NP_416225.1

<400> SEQUENCE: 21
cctttgctga ccatac    16

<210> SEQ ID NO 22
<211> LENGTH: 15
<212> TYPE: DNA
<213> ORGANISM: artificial sequence
<220> FEATURE:
<223> OTHER INFORMATION: Sub-sequences of rbl-1 complementary to known
      target mRNAs (CYGX08010302)
<220> FEATURE:
<221> NAME/KEY: misc_binding
<222> LOCATION: (1)..(15)
<223> OTHER INFORMATION: Potential mRNA target: CaiB corresponding to
      GenBank ID: NP_414580.1

<400> SEQUENCE: 22

```
gacctttgct gacca                                                15
```

<210> SEQ ID NO 23
<211> LENGTH: 14
<212> TYPE: DNA
<213> ORGANISM: artificial sequence
<220> FEATURE:
<223> OTHER INFORMATION: Sub-sequences of rbl-1 complementary to known
      target mRNAs (CYGX 08010303)
<220> FEATURE:
<221> NAME/KEY: misc_binding
<222> LOCATION: (1)..(14)
<223> OTHER INFORMATION: Potential mRNA target: ydgD corresponding to
      GenBank ID: NP_418152.1

<400> SEQUENCE: 23

```
acagttttga tgac                                                 14
```

<210> SEQ ID NO 24
<211> LENGTH: 13
<212> TYPE: DNA
<213> ORGANISM: artificial sequence
<220> FEATURE:
<223> OTHER INFORMATION: Sub-sequences of rbl-1 complementary to known
      target mRNAs (CYGX 08010304)
<220> FEATURE:
<221> NAME/KEY: misc_binding
<222> LOCATION: (1)..(13)
<223> OTHER INFORMATION: Potential mRNA target: ygcQ corresponding to
      GenBank ID: NP_417249.2

<400> SEQUENCE: 24

```
acaattgcga tat                                                  13
```

<210> SEQ ID NO 25
<211> LENGTH: 13
<212> TYPE: DNA
<213> ORGANISM: artificial sequence
<220> FEATURE:
<223> OTHER INFORMATION: Sub-sequences of rbl-1 complementary to known
      target mRNAs (CYGX 08010305)
<220> FEATURE:
<221> NAME/KEY: misc_binding
<222> LOCATION: (1)..(13)
<223> OTHER INFORMATION: Potential mRNA target: ftsH corresponding to
      GenBank: NP_417645.1

<400> SEQUENCE: 25

```
gacctttgct gac                                                  13
```

<210> SEQ ID NO 26
<211> LENGTH: 17
<212> TYPE: DNA
<213> ORGANISM: artificial sequence
<220> FEATURE:
<223> OTHER INFORMATION: Sub-sequences of rbl-1 complementary to known
      target mRNAs (CYGX 08010306)
<220> FEATURE:
<221> NAME/KEY: misc_binding
<222> LOCATION: (1)..(17)
<223> OTHER INFORMATION: Potential mRNA target: ppiB corresponding to
      GenBank ID: NP_415058.1

<400> SEQUENCE: 26

```
tcaacagttt tgatgac                                              17
```

<210> SEQ ID NO 27
<211> LENGTH: 13
<212> TYPE: DNA

```
<213> ORGANISM: artificial sequence
<220> FEATURE:
<223> OTHER INFORMATION: Sub-sequences of rbl-1 complementary to known
      target mRNAs (CYGX 08010307)
<220> FEATURE:
<221> NAME/KEY: misc_binding
<222> LOCATION: (1)..(13)
<223> OTHER INFORMATION: Potential mRNA target: yihl corresponding to
      GenBank ID: NP_418308.1

<400> SEQUENCE: 27
atgacctttg ctg                                                            13

<210> SEQ ID NO 28
<211> LENGTH: 12
<212> TYPE: DNA
<213> ORGANISM: artificial sequence
<220> FEATURE:
<223> OTHER INFORMATION: Sub-sequences of rbl-1 complementary to known
      target mRNAs (CYGX 08010308)
<220> FEATURE:
<221> NAME/KEY: misc_binding
<222> LOCATION: (1)..(12)
<223> OTHER INFORMATION: Potential mRNA target: zntA corresponding to
      GenBank ID: NP_417926.1

<400> SEQUENCE: 28
cagttttgat ga                                                             12

<210> SEQ ID NO 29
<211> LENGTH: 12
<212> TYPE: DNA
<213> ORGANISM: artificial sequence
<220> FEATURE:
<223> OTHER INFORMATION: Sub-sequences of rbl-1 complementary to known
      target mRNAs (CYGX 08010309)
<220> FEATURE:
<221> NAME/KEY: misc_binding
<222> LOCATION: (1)..(12)
<223> OTHER INFORMATION: Potential mRNA target: yicI corresponding to
      GenBank ID: NP_418116.1

<400> SEQUENCE: 29
acctttgctg ac                                                             12

<210> SEQ ID NO 30
<211> LENGTH: 12
<212> TYPE: DNA
<213> ORGANISM: artificial sequence
<220> FEATURE:
<223> OTHER INFORMATION: Sub-sequences of rbl-1 complementary to known
      target mRNAs (CYGX 08010310)
<220> FEATURE:
<221> NAME/KEY: misc_binding
<222> LOCATION: (1)..(12)
<223> OTHER INFORMATION: Potential mRNA target: fhuA corresponding to
      GenBank ID: NP_414692.1

<400> SEQUENCE: 30
ttgctgacca ta                                                             12

<210> SEQ ID NO 31
<211> LENGTH: 12
<212> TYPE: DNA
<213> ORGANISM: artificial sequence
<220> FEATURE:
<223> OTHER INFORMATION: Sub-sequences of rbl-1 complementary to known
      target mRNAs (CYGX 08010311)
<220> FEATURE:
<221> NAME/KEY: misc_binding
<222> LOCATION: (1)..(12)
```

<223> OTHER INFORMATION: Potential mRNA target: rplD corresponding to
      GenBank ID: NP_417778.1

<400> SEQUENCE: 31
tgacctttgc tg                                                           12

<210> SEQ ID NO 32
<211> LENGTH: 12
<212> TYPE: DNA
<213> ORGANISM: artificial sequence
<220> FEATURE:
<223> OTHER INFORMATION: Sub-sequences of rbl-1 complementary to known
      target mRNAs (CYGX 08010312)
<220> FEATURE:
<221> NAME/KEY: misc_binding
<222> LOCATION: (1)..(12)
<223> OTHER INFORMATION: Potential mRNA target: ilvB corresponding to
      GenBank ID: NP_418127.1

<400> SEQUENCE: 32
gttttgatga cc                                                           12

<210> SEQ ID NO 33
<211> LENGTH: 12
<212> TYPE: DNA
<213> ORGANISM: artificial sequence
<220> FEATURE:
<223> OTHER INFORMATION: Sub-sequences of rbl-1 complementary to known
      target mRNAs (CYGX 08010313)
<220> FEATURE:
<221> NAME/KEY: misc_binding
<222> LOCATION: (1)..(12)
<223> OTHER INFORMATION: Potential mRNA target: lepB corresponding to
      GenBank ID: NP_417063.1

<400> SEQUENCE: 33
gcgatatcgt gg                                                           12

<210> SEQ ID NO 34
<211> LENGTH: 12
<212> TYPE: DNA
<213> ORGANISM: artificial sequence
<220> FEATURE:
<223> OTHER INFORMATION: Sub-sequences of rbl-1 complementary to known
      target mRNAs (CYGX 08010314)
<220> FEATURE:
<221> NAME/KEY: misc_binding
<222> LOCATION: (1)..(12)
<223> OTHER INFORMATION: Potential mRNA target: aroK corresponding to
      GenBank ID: NP_417849.1

<400> SEQUENCE: 34
ttgatgacct tt                                                           12

<210> SEQ ID NO 35
<211> LENGTH: 11
<212> TYPE: DNA
<213> ORGANISM: artificial sequence
<220> FEATURE:
<223> OTHER INFORMATION: Sub-sequences of rbl-1 complementary to known
      target mRNAs (CYGX 08010315)
<220> FEATURE:
<221> NAME/KEY: misc_binding
<222> LOCATION: (1)..(11)
<223> OTHER INFORMATION: Potential mRNA target: lepB corresponding to
      GenBank ID: NP_415632.1

<400> SEQUENCE: 35
tggggagtga g                                                            11

<210> SEQ ID NO 36
<211> LENGTH: 11
<212> TYPE: DNA
<213> ORGANISM: artificial sequence
<220> FEATURE:
<223> OTHER INFORMATION: Sub-sequences of rbl-1 complementary to known
      target mRNAs (CYGX 08010316)
<220> FEATURE:
<221> NAME/KEY: misc_binding
<222> LOCATION: (1)..(11)
<223> OTHER INFORMATION: Potential mRNA target: rlpA corresponding to
      GenBank ID: NP_415166.1

<400> SEQUENCE: 36
ttgctgacca t                                                           11

<210> SEQ ID NO 37
<211> LENGTH: 11
<212> TYPE: DNA
<213> ORGANISM: artificial sequence
<220> FEATURE:
<223> OTHER INFORMATION: Sub-sequences of rbl-1 complementary to known
      target mRNAs (CYGX 08010317)
<220> FEATURE:
<221> NAME/KEY: misc_binding
<222> LOCATION: (1)..(11)
<223> OTHER INFORMATION: Potential target: accA corresponding to GenBank
      ID: NP_414727.1

<400> SEQUENCE: 37
ttttgatgac c                                                           11

<210> SEQ ID NO 38
<211> LENGTH: 11
<212> TYPE: DNA
<213> ORGANISM: artificial
<220> FEATURE:
<223> OTHER INFORMATION: Sub-sequences of rbl-1 complementary to known
      target mRNAs (CYGX 08010318)
<220> FEATURE:
<221> NAME/KEY: misc_binding
<222> LOCATION: (1)..(11)
<223> OTHER INFORMATION: Potential mRNA target: pgpA corresponding to
      GenBank ID: NP_414952.1

<400> SEQUENCE: 38
tgatgacctt t                                                           11

<210> SEQ ID NO 39
<211> LENGTH: 14
<212> TYPE: PRT
<213> ORGANISM: artificial sequence
<220> FEATURE:
<223> OTHER INFORMATION: corresponding to bacterial RNA polymerase
      region 1046-1059

<400> SEQUENCE: 39

Lys Ile Thr Gln Gly Asp Asp Leu Ala Pro Gly Val Leu Lys
1               5                   10

<210> SEQ ID NO 40
<211> LENGTH: 16
<212> TYPE: PRT
<213> ORGANISM: artificial sequence
<220> FEATURE:
<223> OTHER INFORMATION: corresponding to bacterial RNA polymerase
      region 970-985

<400> SEQUENCE: 40

-continued

Asp Leu Ser Glu Glu Leu Gln Ile Leu Glu Ala Gly Leu Phe Ser Arg
1               5                   10                  15

<210> SEQ ID NO 41
<211> LENGTH: 13
<212> TYPE: PRT
<213> ORGANISM: artificial sequence
<220> FEATURE:
<223> OTHER INFORMATION: corresponding to bacterial RNA polymerase
      region 718-730

<400> SEQUENCE: 41

Ala Val Ala Val Asp Ser Gly Val Thr Ala Val Ala Lys
1               5                   10

<210> SEQ ID NO 42
<211> LENGTH: 20
<212> TYPE: PRT
<213> ORGANISM: artificial sequence
<220> FEATURE:
<223> OTHER INFORMATION: corresponding to bacterial RNA polymerase
      region 813-832

<400> SEQUENCE: 42

Val Ala Phe Met Pro Trp Asn Gly Tyr Asn Phe Glu Asp Ser Ile Leu
1               5                   10                  15

Val Ser Glu Arg
            20

<210> SEQ ID NO 43
<211> LENGTH: 13
<212> TYPE: PRT
<213> ORGANISM: artificial sequence
<220> FEATURE:
<223> OTHER INFORMATION: corresponding to bacterial RNA polymerase
      region 1047-1059

<400> SEQUENCE: 43

Ile Thr Gln Gly Asp Asp Leu Ala Pro Gly Val Leu Lys
1               5                   10

<210> SEQ ID NO 44
<211> LENGTH: 13
<212> TYPE: PRT
<213> ORGANISM: artificial sequence
<220> FEATURE:
<223> OTHER INFORMATION: corresponding to bacterial RNA polymerase
      region 1170-1182

<400> SEQUENCE: 44

Val Asp Leu Ser Thr Phe Ser Asp Glu Glu Val Met Arg
1               5                   10

<210> SEQ ID NO 45
<211> LENGTH: 14
<212> TYPE: PRT
<213> ORGANISM: artificial sequence
<220> FEATURE:
<223> OTHER INFORMATION: corresponding to bacterial RNA polymerase
      region 86-99

<400> SEQUENCE: 45

Leu Gly Glu Pro Val Phe Asp Val Gln Glu Cys Gln Ile Arg
1               5                   10

<210> SEQ ID NO 46
<211> LENGTH: 10

```
<212> TYPE: PRT
<213> ORGANISM: artificial sequence
<220> FEATURE:
<223> OTHER INFORMATION: corresponding to bacterial RNA polymerase
      region 956-965

<400> SEQUENCE: 46

Ala Leu Glu Ile Glu Glu Met Gln Leu Lys
1               5                   10

<210> SEQ ID NO 47
<211> LENGTH: 10
<212> TYPE: PRT
<213> ORGANISM: artificial sequence
<220> FEATURE:
<223> OTHER INFORMATION: corresponding to bacterial RNA polymerase
      region 163-172

<400> SEQUENCE: 47

Ser Pro Gly Val Phe Phe Asp Ser Asp Lys
1               5                   10

<210> SEQ ID NO 48
<211> LENGTH: 16
<212> TYPE: PRT
<213> ORGANISM: artificial sequence
<220> FEATURE:
<223> OTHER INFORMATION: corresponding to bacterial RNA polymerase
      region 223-238

<400> SEQUENCE: 48

Ala Leu Asn Tyr Thr Thr Glu Gln Ile Leu Asp Leu Phe Phe Glu Lys
1               5                   10                  15

<210> SEQ ID NO 49
<211> LENGTH: 19
<212> TYPE: PRT
<213> ORGANISM: artificial sequence
<220> FEATURE:
<223> OTHER INFORMATION: corresponding to bacterial RNA polymerase
      region 343-363

<400> SEQUENCE: 49

Arg Ile Glu Thr Leu Phe Thr Asn Asp His Gly Pro Tyr Ile Ser Glu
1               5                   10                  15

Thr Leu Arg

<210> SEQ ID NO 50
<211> LENGTH: 16
<212> TYPE: PRT
<213> ORGANISM: artificial sequence
<220> FEATURE:
<223> OTHER INFORMATION: corresponding to bacterial RNA polymerase
      region 390-405

<400> SEQUENCE: 50

Glu Ala Ala Glu Ser Leu Phe Glu Asn Leu Phe Phe Ser Glu Asp Arg
1               5                   10                  15

<210> SEQ ID NO 51
<211> LENGTH: 24
<212> TYPE: PRT
<213> ORGANISM: artificial sequence
<220> FEATURE:
<223> OTHER INFORMATION: corresponding to bacterial RNA polymerase
      region 515-538

<400> SEQUENCE: 51
```

```
Glu Phe Phe Gly Ser Ser Gln Leu Ser Gln Phe Met Asp Gln Asn Asn
1               5                   10                  15

Pro Leu Ser Glu Ile Thr His Lys
            20
```

<210> SEQ ID NO 52
<211> LENGTH: 11
<212> TYPE: PRT
<213> ORGANISM: artificial sequence
<220> FEATURE:
<223> OTHER INFORMATION: corresponding to bacterial RNA polymerase
      region 1008-1018

<400> SEQUENCE: 52

```
Trp Leu Glu Leu Gly Leu Thr Asp Glu Glu Lys
1               5                   10
```

<210> SEQ ID NO 53
<211> LENGTH: 20
<212> TYPE: PRT
<213> ORGANISM: artificial sequence
<220> FEATURE:
<223> OTHER INFORMATION: corresponding to bacterial RNA polymerase
      region 344-363

<400> SEQUENCE: 53

```
Ile Glu Thr Leu Phe Thr Asn Asp Leu Asp His Gly Pro Tyr Ile Ser
1               5                   10                  15

Glu Thr Leu Arg
            20
```

<210> SEQ ID NO 54
<211> LENGTH: 24
<212> TYPE: PRT
<213> ORGANISM: artificial sequence
<220> FEATURE:
<223> OTHER INFORMATION: corresponding to bacterial RNA polymerase
      region 390-413

<400> SEQUENCE: 54

```
Glu Ala Ala Glu Ser Leu Phe Glu Asn Leu Phe Phe Ser Glu Asp Arg
1               5                   10                  15

Tyr Asp Leu Ser Ala Val Gly Arg
            20
```

<210> SEQ ID NO 55
<211> LENGTH: 31
<212> TYPE: PRT
<213> ORGANISM: artificial sequence
<220> FEATURE:
<223> OTHER INFORMATION: corresponding to bacterial RNA polymerase
      region 659-689

<400> SEQUENCE: 55

```
Asp Gln Val Asp Tyr Met Asp Val Ser Thr Gln Gln Val Val Ser Val
1               5                   10                  15

Gly Ala Ser Leu Ile Pro Phe Leu Glu His Asp Asp Ala Asn Arg
            20                  25                  30
```

<210> SEQ ID NO 56
<211> LENGTH: 12
<212> TYPE: PRT
<213> ORGANISM: artificial sequence
<220> FEATURE:
<223> OTHER INFORMATION: corresponding to bacterial RNA polymerase region 731-742

<400> SEQUENCE: 56

Arg Gly Gly Val Val Gln Tyr Val Asp Ala Ser Arg
1               5                   10

<210> SEQ ID NO 57
<211> LENGTH: 13
<212> TYPE: PRT
<213> ORGANISM: artificial sequence
<220> FEATURE:
<223> OTHER INFORMATION: corresponding to bacterial RNA polymerase
      region 1190-1202

<400> SEQUENCE: 57

Gly Met Pro Ile Ala Thr Pro Val Phe Asp Gly Ala Lys
1               5                   10

<210> SEQ ID NO 58
<211> LENGTH: 20
<212> TYPE: PRT
<213> ORGANISM: artificial sequence
<220> FEATURE:
<223> OTHER INFORMATION: corresponding to bacterial RNA polymerase
      region 66-85

<400> SEQUENCE: 58

Ser Val Phe Pro Ile Gln Ser Tyr Ser Gly Asn Ser Glu Leu Gln Tyr
1               5                   10                  15

Val Ser Tyr Arg
            20

<210> SEQ ID NO 59
<211> LENGTH: 19
<212> TYPE: PRT
<213> ORGANISM: artificial sequence
<220> FEATURE:
<223> OTHER INFORMATION: corresponding to bacterial RNA polymerase
      region 423-441

<400> SEQUENCE: 59

Glu Glu Ile Glu Gly Ser Gly Ile Leu Ser Lys Asp Asp Ile Ile Asp
1               5                   10                  15

Val Met Lys

<210> SEQ ID NO 60
<211> LENGTH: 16
<212> TYPE: PRT
<213> ORGANISM: artificial sequence
<220> FEATURE:
<223> OTHER INFORMATION: corresponding to bacterial RNA polymerase
      region 1118-1133

<400> SEQUENCE: 60

Met Asn Ile Gly Gln Ile Leu Glu Thr His Leu Gly Met Ala Ala Lys
1               5                   10                  15

<210> SEQ ID NO 61
<211> LENGTH: 17
<212> TYPE: PRT
<213> ORGANISM: artificial sequence
<220> FEATURE:
<223> OTHER INFORMATION: corresponding to bacterial RNA polymerase
      region 931-947

<400> SEQUENCE: 61

```
Val Pro Asn Gly Val Ser Gly Thr Val Ile Asp Val Gln Val Phe Thr
1               5                   10                  15

Arg

<210> SEQ ID NO 62
<211> LENGTH: 22
<212> TYPE: PRT
<213> ORGANISM: artificial sequence
<220> FEATURE:
<223> OTHER INFORMATION: corresponding to bacterial RNA polymerase
      region 876-897

<400> SEQUENCE: 62

Leu Asp Glu Ser Gly Ile Val Tyr Ile Gly Ala Glu Val Thr Gly Gly
1               5                   10                  15

Asp Ile Leu Val Gly Lys
            20

<210> SEQ ID NO 63
<211> LENGTH: 10
<212> TYPE: PRT
<213> ORGANISM: artificial sequence
<220> FEATURE:
<223> OTHER INFORMATION: corresponding to bacterial RNA polymerase
      region 549-658

<400> SEQUENCE: 63

Ser Lys Gly Glu Ser Ser Leu Phe Ser Arg
1               5                   10

<210> SEQ ID NO 64
<211> LENGTH: 28
<212> TYPE: PRT
<213> ORGANISM: artificial sequence
<220> FEATURE:
<223> OTHER INFORMATION: corresponding to bacterial RNA polymerase
      region 1090-1117

<400> SEQUENCE: 64

Ile Asn Pro Ile Glu Asp Met Pro Tyr Asp Glu Asn Gly Thr Pro Val
1               5                   10                  15

Asp Ile Val Leu Asn Pro Leu Gly Val Pro Ser Arg
            20                  25

<210> SEQ ID NO 65
<211> LENGTH: 8
<212> TYPE: PRT
<213> ORGANISM: artificial sequence
<220> FEATURE:
<223> OTHER INFORMATION: corresponding to bacterial RNA polymerase
      region 1246-1253

<400> SEQUENCE: 65

Leu Asn His Leu Val Asp Asp Lys
1               5

<210> SEQ ID NO 66
<211> LENGTH: 9
<212> TYPE: PRT
<213> ORGANISM: artificial sequence
<220> FEATURE:
<223> OTHER INFORMATION: corresponding to bacterial RNA polymerase
      region 560-568

<400> SEQUENCE: 66

Val Asp His Pro Thr His Tyr Gly Arg
```

```
1               5

<210> SEQ ID NO 67
<211> LENGTH: 20
<212> TYPE: PRT
<213> ORGANISM: artificial sequence
<220> FEATURE:
<223> OTHER INFORMATION: corresponding to bacterial RNA polymerase
      region 747-766

<400> SEQUENCE: 67

Val Asn Glu Asp Glu Met Tyr Pro Gly Glu Ala Gly Ile Asp Ile Tyr
1               5                   10                  15

Asn Leu Thr Lys
            20

<210> SEQ ID NO 68
<211> LENGTH: 10
<212> TYPE: PRT
<213> ORGANISM: artificial sequence
<220> FEATURE:
<223> OTHER INFORMATION: corresponding to bacterial RNA polymerase
      region 902-911

<400> SEQUENCE: 68

Gly Glu Thr Gln Leu Thr Pro Glu Glu Lys
1               5                   10

<210> SEQ ID NO 69
<211> LENGTH: 10
<212> TYPE: PRT
<213> ORGANISM: artificial sequence
<220> FEATURE:
<223> OTHER INFORMATION: corresponding to bacterial RNA polymerase
      region 380-389

<400> SEQUENCE: 69

Met Met Arg Pro Gly Glu Pro Pro Thr Arg
1               5                   10

<210> SEQ ID NO 70
<211> LENGTH: 8
<212> TYPE: PRT
<213> ORGANISM: artificial sequence
<220> FEATURE:
<223> OTHER INFORMATION: corresponding to bacterial RNA polymerase
      region 215-222

<400> SEQUENCE: 70

Leu Pro Ala Thr Ile Ile Leu Arg
1               5

<210> SEQ ID NO 71
<211> LENGTH: 35
<212> TYPE: DNA
<213> ORGANISM: artificial sequence
<220> FEATURE:
<223> OTHER INFORMATION: rb1-1 fragment sequence, residues 1-35

<400> SEQUENCE: 71
tttgatgacc tttgctgacc atacaattgc gatat                              35

<210> SEQ ID NO 72
<211> LENGTH: 30
<212> TYPE: DNA
<213> ORGANISM: artificial sequence
<220> FEATURE:
```

<223> OTHER INFORMATION: rb1-1 fragment sequence, residues 1-30

<400> SEQUENCE: 72
tttgatgacc tttgctgacc atacaattgc                                                30

<210> SEQ ID NO 73
<211> LENGTH: 25
<212> TYPE: DNA
<213> ORGANISM: artificial sequence
<220> FEATURE:
<223> OTHER INFORMATION: rb1-1 fragment sequence, residues 1-25

<400> SEQUENCE: 73
tttgatgacc tttgctgacc ataca                                                     25

<210> SEQ ID NO 74
<211> LENGTH: 20
<212> TYPE: DNA
<213> ORGANISM: artificial sequence
<220> FEATURE:
<223> OTHER INFORMATION: rb1-1 fragment  sequence, residues 1-20

<400> SEQUENCE: 74
tttgatgacc tttgctgacc                                                           20

<210> SEQ ID NO 75
<211> LENGTH: 15
<212> TYPE: DNA
<213> ORGANISM: artificial sequence
<220> FEATURE:
<223> OTHER INFORMATION: rb1-1 fragment sequence, residues 1-15

<400> SEQUENCE: 75
tttgatgacc tttgc                                                                15

<210> SEQ ID NO 76
<211> LENGTH: 35
<212> TYPE: DNA
<213> ORGANISM: artificial sequence
<220> FEATURE:
<223> OTHER INFORMATION: rb1-1 fragment sequence, residues 6-40

<400> SEQUENCE: 76
tgacctttgc tgaccataca attgcgatat cgtgg                                          35

<210> SEQ ID NO 77
<211> LENGTH: 30
<212> TYPE: DNA
<213> ORGANISM: artificial sequence
<220> FEATURE:
<223> OTHER INFORMATION: rb1-1 fragment sequence, residues 11-40

<400> SEQUENCE: 77
tttgctgacc atacaattgc gatatcgtgg                                                30

<210> SEQ ID NO 78
<211> LENGTH: 25
<212> TYPE: DNA
<213> ORGANISM: artificial sequence
<220> FEATURE:
<223> OTHER INFORMATION: rb1-1 fragment sequence, residues 16-40

<400> SEQUENCE: 78
tgaccataca attgcgatat cgtgg                                                     25

```
<210> SEQ ID NO 79
<211> LENGTH: 20
<212> TYPE: DNA
<213> ORGANISM: artificial sequence
<220> FEATURE:
<223> OTHER INFORMATION: rb1-1 fragment sequence, residues 12-40

<400> SEQUENCE: 79
atacaattgc gatatcgtgg                                               20

<210> SEQ ID NO 80
<211> LENGTH: 15
<212> TYPE: DNA
<213> ORGANISM: artificial sequence
<220> FEATURE:
<223> OTHER INFORMATION: rb1-1 fragment sequence, residues 26-40

<400> SEQUENCE: 80
attgcgatat cgtgg                                                    15

<210> SEQ ID NO 81
<211> LENGTH: 10
<212> TYPE: DNA
<213> ORGANISM: artificial sequence
<220> FEATURE:
<223> OTHER INFORMATION: rb1-1 fragment sequence, residues 21-30

<400> SEQUENCE: 81
atacaattgc                                                          10

<210> SEQ ID NO 82
<211> LENGTH: 12
<212> TYPE: DNA
<213> ORGANISM: artificial sequence
<220> FEATURE:
<223> OTHER INFORMATION: rb1-1 fragment sequence, residues 21-32

<400> SEQUENCE: 82
atacaattgc ga                                                       12

<210> SEQ ID NO 83
<211> LENGTH: 14
<212> TYPE: DNA
<213> ORGANISM: artificial sequence
<220> FEATURE:
<223> OTHER INFORMATION: rb1-1 fragment sequence, residues 21-34

<400> SEQUENCE: 83
atacaattgc gata                                                     14

<210> SEQ ID NO 84
<211> LENGTH: 16
<212> TYPE: DNA
<213> ORGANISM: artificial sequence
<220> FEATURE:
<223> OTHER INFORMATION: rb1-1 fragment sequence, residues 21-36

<400> SEQUENCE: 84
atacaattgc gatatc                                                   16

<210> SEQ ID NO 85
<211> LENGTH: 18
<212> TYPE: DNA
<213> ORGANISM: artificial sequence
<220> FEATURE:
<223> OTHER INFORMATION: rb1-1 fragment 21-38
```

```
<400> SEQUENCE: 85
atacaattgc gatatcgt                                                    18

<210> SEQ ID NO 86
<211> LENGTH: 23
<212> TYPE: DNA
<213> ORGANISM: artificial sequence
<220> FEATURE:
<223> OTHER INFORMATION: double stranded comprising the sequences
      5'BamHI EcoRI(m)

<400> SEQUENCE: 86
gatccactag tccagtgtgg tgt                                              23

<210> SEQ ID NO 87
<211> LENGTH: 24
<212> TYPE: DNA
<213> ORGANISM: artificial sequence
<220> FEATURE:
<223> OTHER INFORMATION: double stranded oligo comprising the sequence
      3'-BamHIEcoRI(m)

<400> SEQUENCE: 87
gaattacacc acactggact agtg                                             24
```

What is claimed is:

1. A single-stranded DNA expression cassette comprising in 5' to 3' order, a promoter, a primer binding site and an expression termination sequence, having one or more of the following sequences inserted between the promoter and the primer binding site:

```
                                                  [SEQ ID NO: 18]
TTTGATGACC TTTGCTGACC ATACAATTGC GATATCGTGG

[SEQ ID NO: 71]
TTTGATGACC TTTGCTGACC ATACAATTGC GATAT

[SEQ ID NO: 72]
TTTGATGACC TTTGCTGACC ATACAATTGC

[SEQ ID NO: 76]
TGACCTTTGC TGACCATACA ATTGCGATAT CGTGG

[SEQ ID NO: 77]
TTTGCTGACC ATACAATTGC GATATCGTGG

[SEQ ID NO: 78]
TGACCATACA ATTGCGATAT CGTGG

[SEQ ID NO: 79]
ATACAATTGC GATATCGTGG

[SEQ ID NO: 84]
ATACAATTGC GATATC

[SEQ ID NO: 85]
ATACAATTGC GATATCGT.
```

2. An expression vector comprising the expression cassette of claim claim 1.

3. The expression cassette of claim 1, wherein the promoter is an inducible promoter.

4. The expression cassette of claim 2, further comprising a gene coding for a reverse transcriptase.

5. The expression cassette of claim 4, wherein the primer binding site is recognized by the reverse transcriptase in the presence of tRNAVal.

6. A cell having the expression vector of claim 2 introduced therein.

7. A conjugate comprising a peptide and a single-stranded DNA expression cassette comprising in 5' to 3' order, a promoter, a primer binding site and an expression termination sequence, having one or more of the following sequences inserted between the promoter and the primer binding site:

```
                                                  [SEQ ID NO: 18]
TTTGATGACC TTTGCTGACC ATACAATTGC GATATCGTGG

[SEQ ID NO: 71]
TTTGATGACC TTTGCTGACC ATACAATTGC GATAT

[SEQ ID NO: 72]
TTTGATGACC TTTGCTGACC ATACAATTGC

[SEQ ID NO: 76]
TGACCTTTGC TGACCATACA ATTGCGATAT CGTGG

[SEQ ID NO: 77]
TTTGCTGACC ATACAATTGC GATATCGTGG

[SEQ ID NO: 78]
TGACCATACA ATTGCGATAT CGTGG

[SEQ ID NO: 79]
ATACAATTGC GATATCGTGG

[SEQ ID NO: 84]
ATACAATTGC GATATC

[SEQ ID NO: 85]
ATACAATTGC GATATCGT.
```

8. The conjugate of claim 7 wherein the peptide is a bacterial targeting peptide or a homolog or derivative thereof.

9. A pharmaceutical composition comprising a pharmacologically acceptable diluent, adjuvant, aerosol or carrier and an expression cassette, itself comprising a sequence as listed below:

```
                                [SEQ ID NO: 71]
TTTGATGACC TTTGCTGACC ATACAATTGC GATAT

[SEQ ID NO: 72]
TTTGATGACC TTTGCTGACC ATACAATTGC

[SEQ ID NO: 76]
TGACCTTTGC TGACCATACA ATTGCGATAT CGTGG

[SEQ ID NO: 77]
TTTGCTGACC ATACAATTGC GATATCGTGG

[SEQ ID NO: 78]
TGACCATACA ATTGCGATAT CGTGG

[SEQ ID NO: 79]
ATACAATTGC GATATCGTGG

[SEQ ID NO: 84]
ATACAATTGC GATATC

[SEQ ID NO: 85]
ATACAATTGC GATATCGT.
```

10. A method for inhibiting RNA polymerase activity comprising contacting an RNA polymerase with the expression cassette of claim 1.

11. A method for inhibiting growth of a pathogenic microorganism, killing a pathogenic microorganism, or inhibiting synthesis or secretion of a toxin by a pathogenic microorganism, comprising contacting the pathogenic microorganism with the expression vector of claim 2.

12. The method of claim 11, wherein the pathogenic microorganism comprises a causative agent of sepsis.

\* \* \* \* \*